US009924956B2

(12) United States Patent
Baumgartner (10) Patent No.: US 9,924,956 B2
(45) Date of Patent: Mar. 27, 2018

(54) ALIGNMENT DEVICE FOR DISTAL TARGETING (75) Inventor: Adrian Baumgartner, Oberdorf (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 1395 days.

(21) Appl. No.: 13/351,687

(22) Filed: Jan. 17, 2012

(65) Prior Publication Data

US 2013/0018381 A1 Jan. 17, 2013

Related U.S. Application Data (60) Provisional application No. 61/437,182, filed on Jan. 28, 2011.

(51) Int. Cl.
*A61B 17/17* (2006.01)

(52) U.S. Cl.
CPC .......... *A61B 17/1707* (2013.01); *A61B 17/17* (2013.01); *A61B 17/1717* (2013.01); *A61B 17/1725* (2013.01)

(58) Field of Classification Search
CPC . A61B 17/17; A61B 17/1707; A61B 17/1717; A61B 17/1725
USPC ............................... 606/62–64, 86 R, 96–98
See application file for complete search history.

(56) References Cited

U.S. PATENT DOCUMENTS

| 5,127,913 | A | 7/1992 | Thomas | |
|---|---|---|---|---|
| 5,514,145 | A * | 5/1996 | Durham et al. | 606/96 |
| 5,584,838 | A | 12/1996 | Rona et al. | |
| 6,162,228 | A | 12/2000 | Durham | |
| 7,029,478 | B2 | 4/2006 | Hollstein et al. | |
| 7,060,075 | B2 * | 6/2006 | Govari et al. | 606/98 |
| 7,753,913 | B2 | 7/2010 | Szakelyhidi et al. | |
| 7,785,330 | B2 * | 8/2010 | Sherman et al. | 606/96 |
| 2004/0138671 | A1 | 7/2004 | Zander et al. | |
| 2008/0058829 | A1 | 3/2008 | Buscher et al. | |
| 2010/0249782 | A1 * | 9/2010 | Durham | 606/62 |

FOREIGN PATENT DOCUMENTS

| EP | 0 135 804 | 4/1985 |
|---|---|---|
| EP | 1 902 679 | 3/2008 |
| WO | 93/02626 | 2/1993 |
| WO | 2009/109371 | 9/2009 |
| WO | 2010/123879 | 10/2010 |

* cited by examiner

*Primary Examiner* — Larry E Waggle, Jr.
(74) *Attorney, Agent, or Firm* — Fay Kaplun & Marcin, LLP (57) ABSTRACT

A device is for aligning an aiming hole of an aiming device with a locking hole of an intramedullary nail. The device includes a sensing unit sized and shaped for insertion through an aiming hole of an aiming device attachable to an intramedullary nail. The sensing unit detects a magnetic field produced by a magnet and outputs an alignment signal based on a magnetic field parameter at first and second locations relative to the magnet.

24 Claims, 9 Drawing Sheets

ALIGNMENT DEVICE FOR DISTAL TARGETING

PRIORITY CLAIM

The present application claims priority to U.S. Provisional Application Ser. No. 61/437,182 filed on Jan. 28, 2011 and entitled "Alignment Device for Distal Targeting," the entire disclosure of which is incorporated herein by reference.

BACKGROUND

Intramedullary nails are often inserted into the medullary canals of long bones and fixed therein via locking screws inserted through locking holes of the nails to treat fractures. An aiming device including aiming holes may be attached to the intramedullary nail prior to insertion with aiming holes of the aiming device substantially aligned with the locking holes to guide a drill and/or the locking screws to the locking holes. Insertion of the intramedullary nail into the bone, however, often results in deformation of the intramedullary nail moving the locking holes out of alignment with the aiming holes. Currently, a surgeon or other user may utilize an X-ray image to determine an adjustment required to align the aiming holes of the aiming device with the locking holes of the intramedullary nail.

SUMMARY OF THE INVENTION

The present invention relates to a device for aligning an aiming hole of an aiming device with a locking hole of an intramedullary nail. The device includes a sensing unit sized and shaped for insertion through an aiming hole of an aiming device attachable to an intramedullary nail. The sensing unit detects a magnetic field produced by a magnet and outputs an alignment signal based on a magnetic field parameter at first and second locations relative to the magnet

DETAILED DESCRIPTION

The present invention may be further understood with reference to the following description and the appended drawings, wherein like elements are referred to with the same reference numerals. The present invention relates to devices for treating bones and, in particular, to a device ensuring alignment of one or more aiming holes of an aiming device with corresponding locking holes of an intramedullary nail. Exemplary embodiments of the present invention describe a magnet inserted into the intramedullary nail and at least one sensor detecting the magnetic field produced by the magnet to determine a displacement of the sensor relative to the magnet. The displacement is then used to adjust the aiming device so that aiming holes thereof align with the locking holes. It should be noted that the terms "proximal" and "distal" as used herein refer to a direction toward (proximal) and away from (distal) a user of the device.

Figure 1:
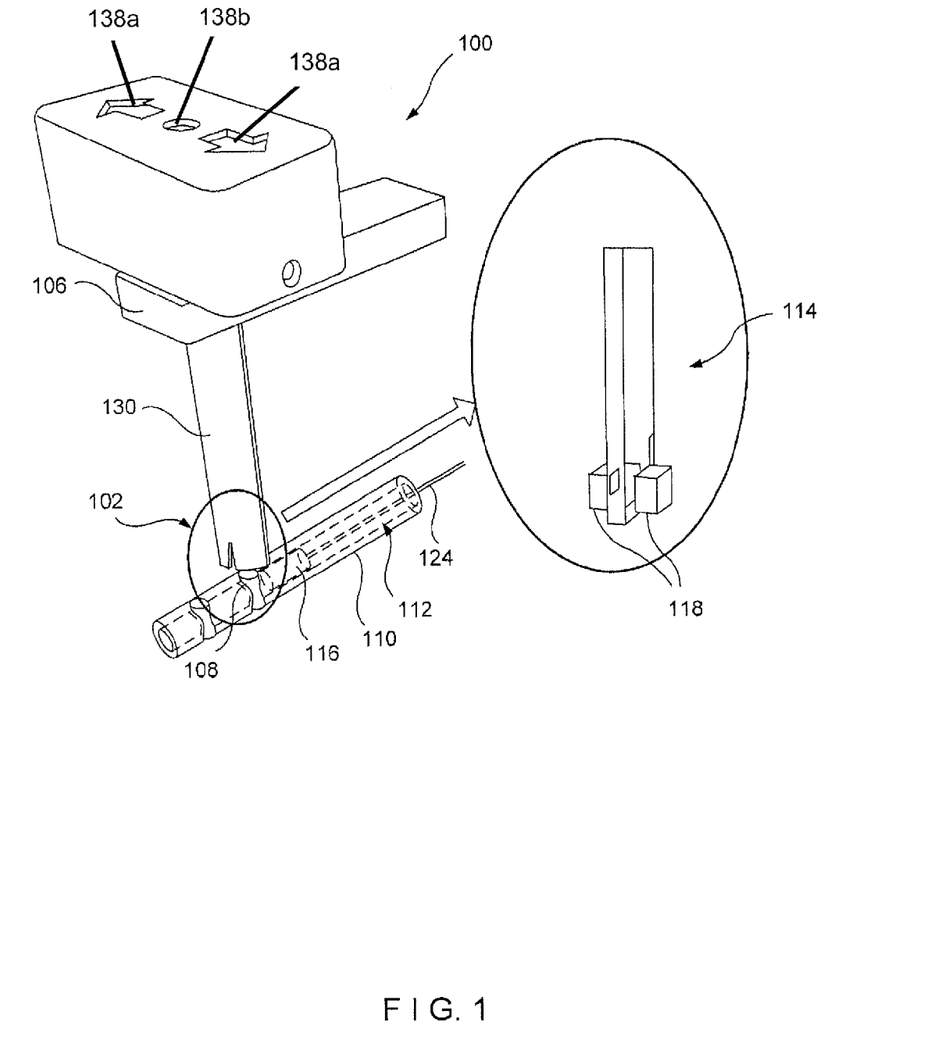
FIG. 1 shows a perspective view of a system according to an exemplary embodiment of the present invention.
Figure 2:
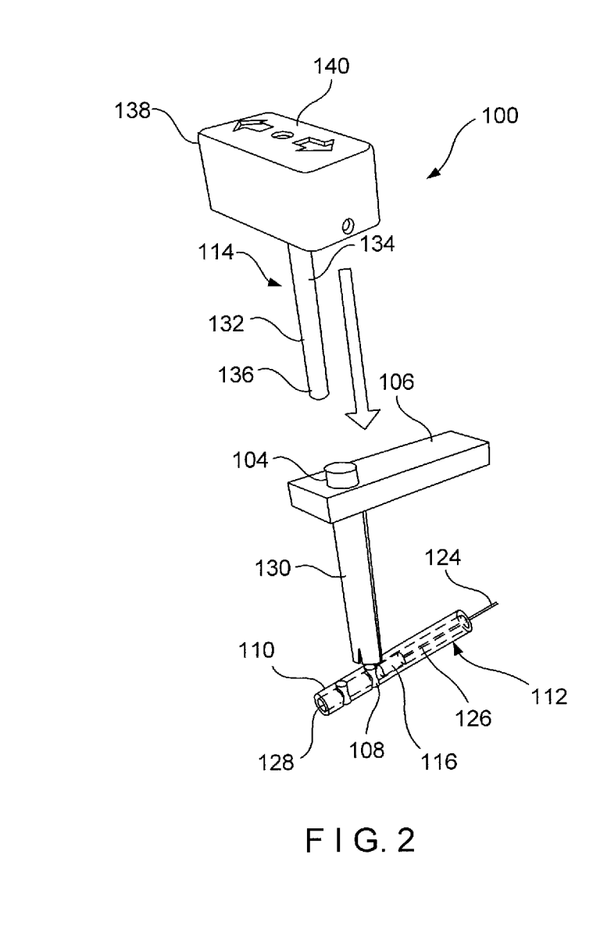
FIG. 2 shows another perspective view of the system of FIG. 1.
Figure 3:
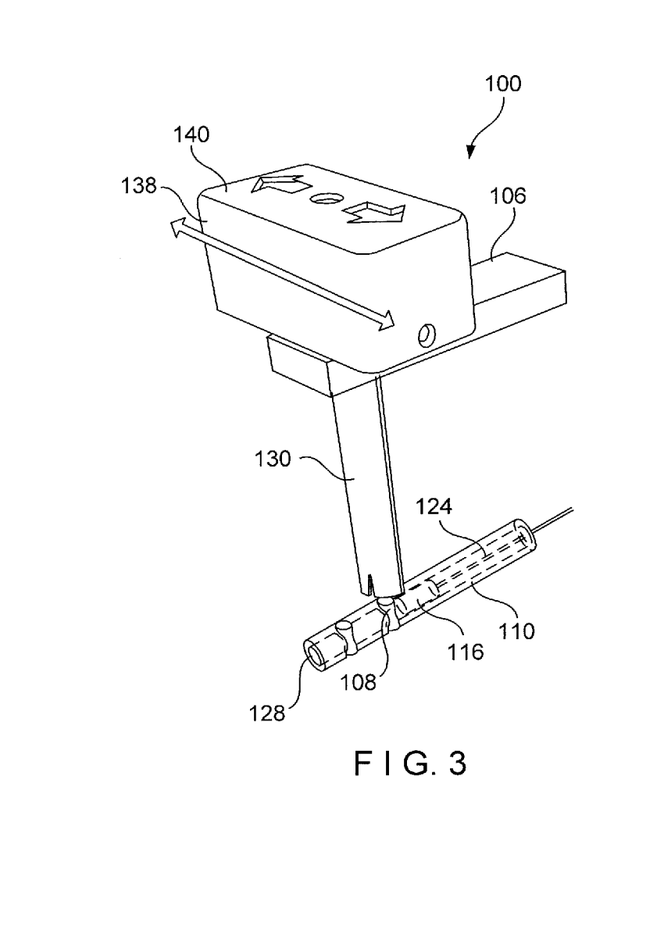
FIG. 3 shows yet another perspective view of the system of FIG. 1.
Figure 4:
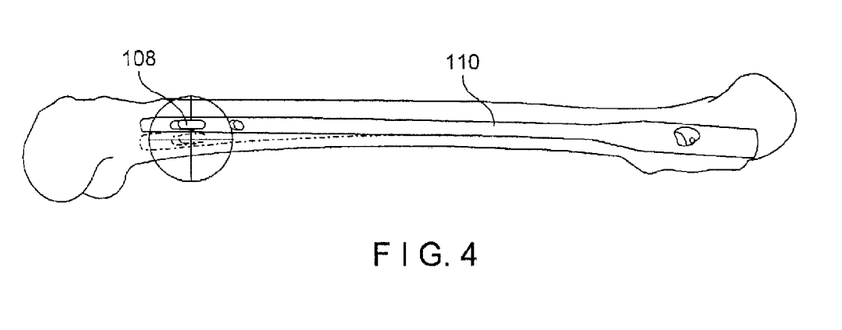
FIG. 4 shows a deformation of an intramedullary nail upon insertion into a bone.
Figure 5:
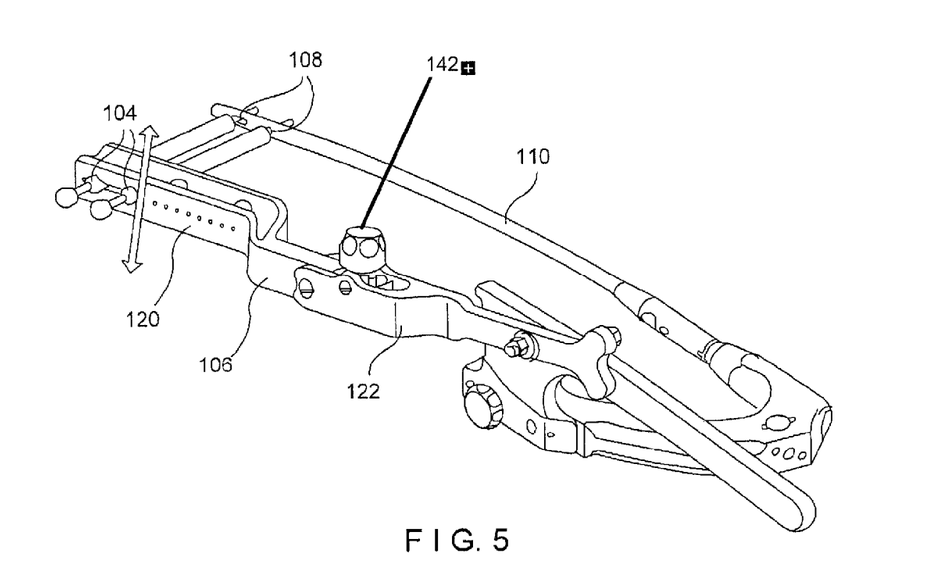
FIG. 5 shows an aiming device coupled to an intramedullary nail according to the system of FIG. 1.

As shown in FIGS. 1-9, a system 100 according to an exemplary embodiment of the present invention comprises an alignment guiding device 102 for aligning of an aiming hole 104 of an aiming device 106 with a locking hole 108 of an intramedullary nail 110. The locking hole 108 extends transversely through, for example, a distal portion of the intramedullary nail 110 and is sized and shaped to receive a bone fixation element therethrough. The aiming device 106 is coupled to the intramedullary nail 110 such that the aiming hole 104 and the locking hole 108 are substantially aligned (i.e., a central axis of the aiming hole 104 is coaxial with a central axis of the locking hole 108) so that a drill and/or bone fixation element may be guided into the locking hole 108 via, for example, a guide sleeve 130. Upon insertion of the intramedullary nail 110 into a medullary canal of a bone, however, the intramedullary nail 110 may deform such that the central axis of the locking hole 108 is no longer aligned with the central axis of the aiming hole 104, as shown in FIG. 4. The alignment guiding device 102, as shown in FIGS. 1-2, comprises a first component 112 including a magnet 116 inserted into a longitudinal channel 128 of the intramedullary nail 110 proximate to the locking hole 108 and a second component 114 including a sensing unit 118 inserted through the aiming hole 104 and/or guide sleeve 130 to determine a displacement of the aiming hole 104 relative to the locking hole 108. The alignment guiding device 102 indicates an alignment of the aiming hole 104 and locking hole 108 and/or a required adjustment of the aiming device 106 to align the aiming hole 104 with the locking hole 108. As shown in FIG. 5, the aiming device 106 may be adjusted by, for example, pivoting a distal portion 120 thereof, which includes the aiming hole 104 extending therethrough, relative to a proximal portion 122 thereof. The distal portion 120 may be moved until the alignment guiding device 102 indicates that the aiming hole 104 and the locking hole 108 have been correctly realigned. It will be understood by those of skill in the art that the aiming device 106 may include any number of aiming holes 104, each of which may be aligned with a respective locking hole 108 in the intramedullary nail 110 using the alignment guiding device 102, as described in further detail below.

The first component 112 of the alignment guiding device 102, as shown in FIGS. 1-3, includes a rod 124 extending longitudinally from a proximal end (not shown) to a distal end 126 attached to a magnet 116. The magnet 116 and rod 124 are sized and shaped to be slid through a channel 128 of the intramedullary nail 110 and positioned in or proximate to a selected one of the locking holes 108. The magnet 116 is positioned within the channel 128, for example, intersecting with the central axis of the selected locking hole 108 (e.g., positioned between openings of the selected locking hole 108 on opposite sides of the nail 110). Alternatively, the magnet 116 may be positioned near the locking hole 108, immediately proximal or distal to the openings defining the locking hole 108. In the preferred embodiment, the magnet 116 is positioned immediately proximal to the locking hole 108 so that it does not need to be removed before the surgeon drills a hole through the bone and the locking hole 108. The magnet 116 may be, for example, a bar magnet oriented with poles axially aligned with a longitudinal axis of the rod 124. In one exemplary embodiment, the magnet 116 may be approximately 10 mm long and 4 mm wide. It will be understood by those of skill in the art, however, that the magnet 116 may be any of a variety of shapes and sizes so long as the magnet 116 is insertable through the channel 128 of the intramedullary nail 110. A length of the rod 124 is selected to correspond to a length of the intramedullary nail 110 such that when the first component 112 is inserted into the nail 110, the magnet 116 may be inserted within the channel 128 to one or more desired positions corresponding to the locking holes 108. In another embodiment, the rod 124 may include markings along a length thereof to indicate lengths to which the rod 124 should be inserted into the nail 110 to achieve desired positions relative to the locking holes 108.

The second component 114 includes a probe 132 extending longitudinally from a proximal end 134 to a distal end 136 and including the sensing unit 118. For example, the sensing unit 118 may be mounted to a printed circuit board (PCB) 133 which is fixed within the probe 132. The second component 114 may also include an indicator 138 at the proximal end 134 of the probe 132. The probe 132 is sized and shaped to be inserted through a guide sleeve 130 which is inserted through the aiming hole 104 of the aiming device 106. The guide sleeve 130 may be, for example, a drill sleeve or a protective sleeve used during drilling of the bone and/or insertion of bone fixation elements into the nail 110. The guide sleeve 130 may be pushed through the skin and soft tissue of the patient until a distal end thereof contacts the bone. A length of the probe 132 is selected such that, in an operative position, the distal end 136 thereof is adjacent to or extends distally beyond a distal end of the guide sleeve 130 so that, when the guide sleeve 130 is positioned against the bone, the sensing unit 118 is as close to the magnet 116 within the nail 110 as possible. For example, the length of the probe 132 may be approximately 160 mm. A width of the probe 132 is selected to permit slidable insertion of the probe 132 through the guide sleeve 130, while ensuring that a longitudinal axis of the probe 132 is coaxial with a longitudinal axis of the guide sleeve 130. For example, the probe 132 may have a width (e.g., diameter) of approximately 8 mm. It will be understood by those of skill in the art, however, that probe 132 may have any of a variety of lengths and widths so long as the probe 132 coaxially insertable through the aiming hole 104 and/or the guide sleeve 130.

The indicator 138 includes an input device which receives alignment information from the sensing unit 118 and a display 140 which displays an alignment and/or misalignment of the aiming hole 104 relative to the locking hole 108. For example, the display 140 may include two direction indicators 138a and an alignment indicator 138b. The direction indicator 138a may be a pointer or arrow indicating a direction in which the aiming device 106 should be moved to align the aiming hole 104 with the locking hole 110. The alignment indicator 138b may be, for example, a shape or symbol, which indicates when an alignment of the aiming hole 104 and the locking hole 108 has been achieved. The display 140 may receive the alignment information from the input device to, for example, illuminate one of the direction indicators or alignment indicators to show whether an adjustment of the aiming device 106 is necessary and, if so, in which direction the aiming device 108 should be moved. Although the display 140 is described as including illuminatable indicators, it will be understood by those of skill in the art that any of a variety of display features may be used so long as the display 140 indicates an alignment between the aiming hole 104 and the locking hole 108.

Figure 6:
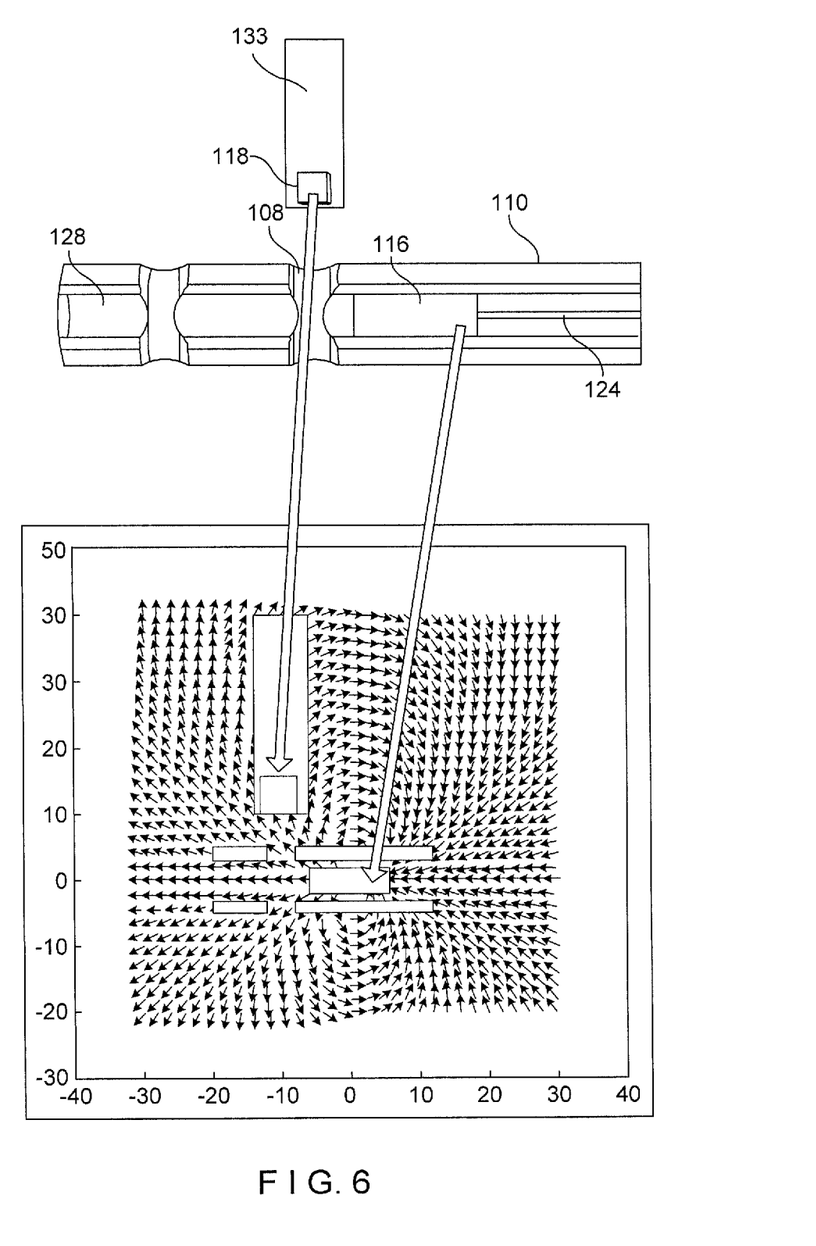
FIG. 6 shows a cross-section side view of the system of FIG. 1.
Figure 7:
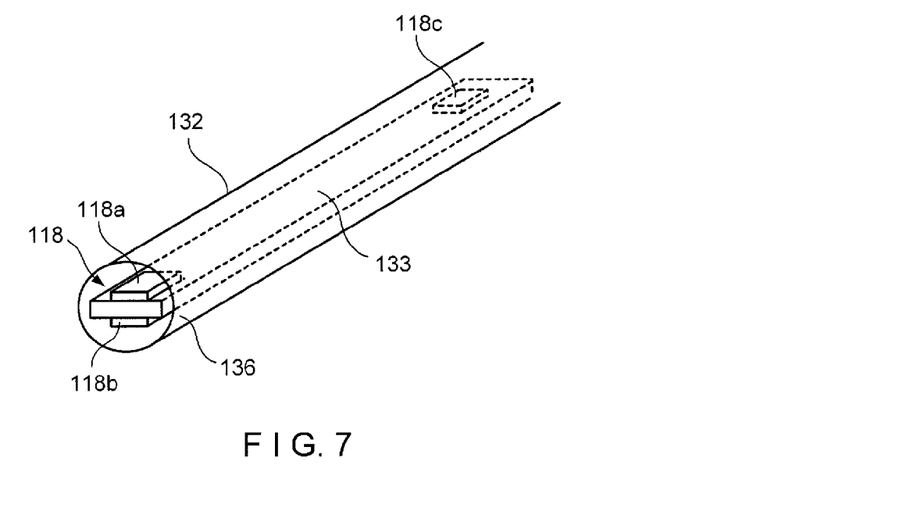
FIG. 7 shows a perspective view of a sensing unit according to the system of FIG. 1.

As shown in FIG. 6, the sensing unit 118 detects a magnetic field generated by the magnet 116. The sensing unit 118 may be arranged within the probe 132 in any of a variety of ways. In one exemplary embodiment, as shown in FIG. 7, the sensing unit 118 includes first and second sensors 118a, 118b, respectively, to provide alignment information and a third sensor 118c for identifying the presence of anomalies. The first and second sensors 118a, 118b form a sensing pair at the distal end 136 of the probe 132 on opposite sides of the probe 132 and at the same longitudinal position longitudinally along the probe 132. For example, the first and second sensors 118a, 118b may be soldered to the PCB 133 at the same longitudinal position and on opposing sides thereof. The PCB 133 may be fixed within the probe 132 such that the sensing unit 118 is positioned at the distal end 136 thereof. The third sensor 118c may be positioned on the PCB 133 proximally of the first and second sensors 118a, 118b. The third sensor 118c is positioned so that its central axis is aligned with a central axis of the PCB 133.

The first and second sensors 118a, 118b are configured to sense a parameter of a magnetic field generated by the magnet 116 (e.g., such as a field vector or field strength) at different locations. The sensors 118a, 118b may be one-dimensional sensors, two-dimensional sensors, three-dimensional sensors, or any combination thereof. The first and second sensors 118a, 118b, are arranged to output a signal corresponding to the magnetic field parameters in two or three dimensions. These signals from the sensors 118a, 118b are received by the input device of the indicator 138 and analyzed to determine a required adjustment of the aiming device 106 to achieve the desired alignment with the selected locking hole 108. This information may then be shown on the display 140. The third sensor 118c may be affected by the presence of anomalies or magnetic artifacts in or around the sensing space that could interfere with the magnetic field from the magnet 116 in the intramedullary nail 110. The third sensor 118c outputs a signal that corresponds to a magnetic field parameter, for example, the magnetic field strength. In a first situation where no anomalies are present, the third sensor outputs a signal indicating a desired level of a parameter is reached, for example, maximum field strength, when sensors 118a, 118b have achieved the desired alignment. In a second situation where an anomaly is present, when sensors 118a, 118b indicate that a desired alignment has been achieved, the third sensor 118c may indicate that the desired level of the parameter has not been reached. In the second situation the aiming device 106 may output a signal indicating an anomaly is present since there is a discrepancy between the desired alignment signal and desired level signal. Thus, the third sensor 118c is an indicator used to determine whether a reliable sensing is possible. For example, when the third sensor 118c identifies the presence of anomalies, it may be determined that a reliable sensing is not possible.

Figure 8:
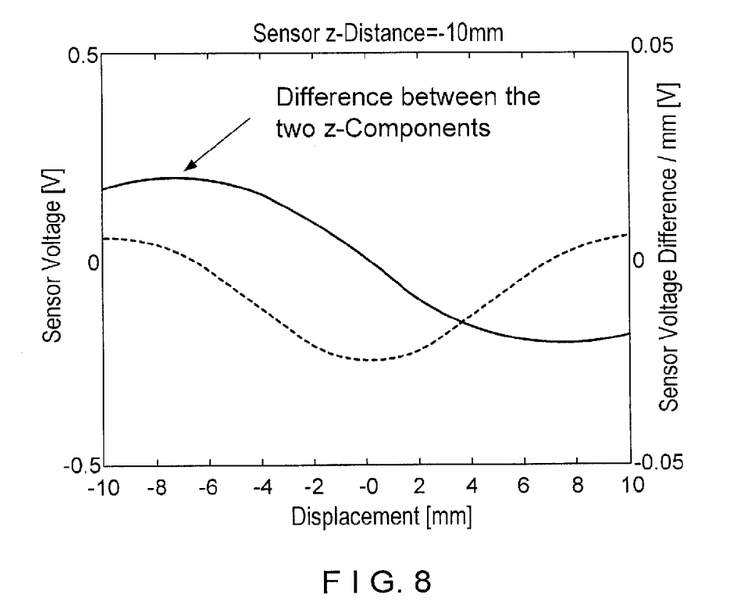
FIG. 8 shows a graph illustrating an exemplary differential voltage sensed by the sensor of FIG. 7.

FIG. 8 shows an exemplary difference in field components detected by the first and second sensors 118a, 118b. The aiming device 106 is adjusted, as directed by the indicator 138, until each of the sensors 118a, 118b detects a field having the same vector or strength in opposing directions indicating alignment with the magnet 116—i.e., alignment of the aiming hole 104 and the locking hole 108. Thus, alignment may be indicated when a difference between the signals outputted by the first and second sensors 118a, 118b is substantially zero (i.e., less than a predetermined threshold level). However, other analyses via, for example, adding, multiplying, dividing the signals of the first and second sensors 118a, 118b may be conducted as required.

Figure 9:
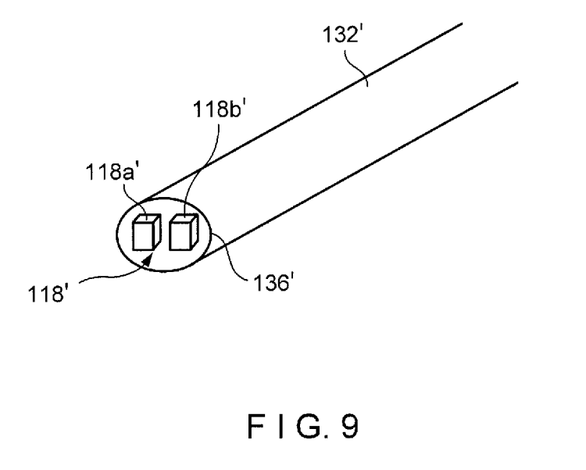
FIG. 9 shows a perspective view of a sensing unit according to an alternate embodiment of the present invention.

In another embodiment, as shown in FIG. 9, a sensing unit 118' includes a first and second sensor 118a', 118b' may be arranged in a substantially similar manner at a distal end 136' of a probe 132'. In particular, the first and second sensors 118a', 118b' are arranged on opposing sides of a PCB 133' at the same longitudinal position therealong. The PCB 133' is fixed within the probe 132'. The first and second sensors 118a', 118b', however, are one-dimensional sensors such that the sensors 118a', 118b' measure a distance of a field component from the distal end 136' of the probe 132'. A differential voltage indicates a direction and a correct alignment thereof.

Figure 10:
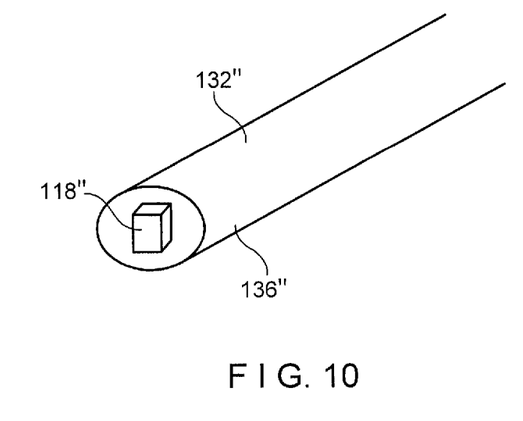
FIG. 10 shows a perspective view of a sensing unit according to yet another alternate embodiment of the present invention.

In another embodiment, as shown in FIG. 10, a sensing unit includes a single sensor 118" within a distal end 136" of a probe 132". Since there is only one sensor 118", a differential signal (e.g., differential of voltage) cannot be generated. Thus, in this embodiment, the aiming device 106, including the probe 132" and the sensor 118" inserted through the aiming hole 104, is moved until the indicator 138 indicates that the aiming hole 104 is aligned with the locking hole 108. When the probe 132" is moved, the differential signal is tracked on a discrete basis according to a unit of time to determine a correct alignment.

According to an exemplary surgical technique using the system 100, the aiming device 106 is attached to the intramedullary nail 110 such that the aiming hole 104 is substantially aligned with the locking hole 108. The intramedullary nail 110 is then inserted into the medullary canal of the bone. Upon insertion into the bone, it will be understood by those of skill in the art that the intramedullary nail 110 may deform such that the locking hole 108 is no longer aligned with the aiming hole 104. The aiming device 106 must be adjusted to compensate for any deformation. To determine the required adjustment of the aiming device 106, the first component 112 of the alignment guiding device 102 is inserted into the channel 128 of the intramedullary nail 110 such that the magnet 116 is positioned proximate the locking hole 108, as described above. The probe 132 of the second component 114 is then inserted through a guide sleeve 130, which has been inserted through the aiming hole 104, until the sensing unit 118 is positioned proximate a distal end of the guide sleeve 130 adjacent the skin close to the expected position of the locking hole 108. The sensing unit 118 may be any of the sensor configurations described above.

The sensing unit 118 detects from within the body a magnetic field produced by the magnet 116 to determine whether the sensing unit 118 is in alignment with the magnet 116—i.e., whether the aiming hole 104 is aligned with the locking hole 108. The indicator 138 indicates to the user whether the aiming hole 104 and the locking hole 108 are in alignment. If the aiming hole 104 and the locking hole 108 are not aligned, the user may move at least a portion of the aiming device 106 relative to the intramedullary nail 110 until the desired alignment is achieved. For example, the user may move the distal portion 120 of the aiming device 106 relative to the proximal portion 122 by loosening a knob 142, which couples the distal portion 120 to the proximal portion 122, to pivot the distal portion 120 about a pin portion of knob 142. The aiming device 106 is moved until the indicator 138 indicates that the aiming hole 104 and the locking hole 108 are in alignment. The knob 142 may then be tightened to maintain the alignment position of the aiming device 106 relative to the intramedullary nail 110.

Figure 11:
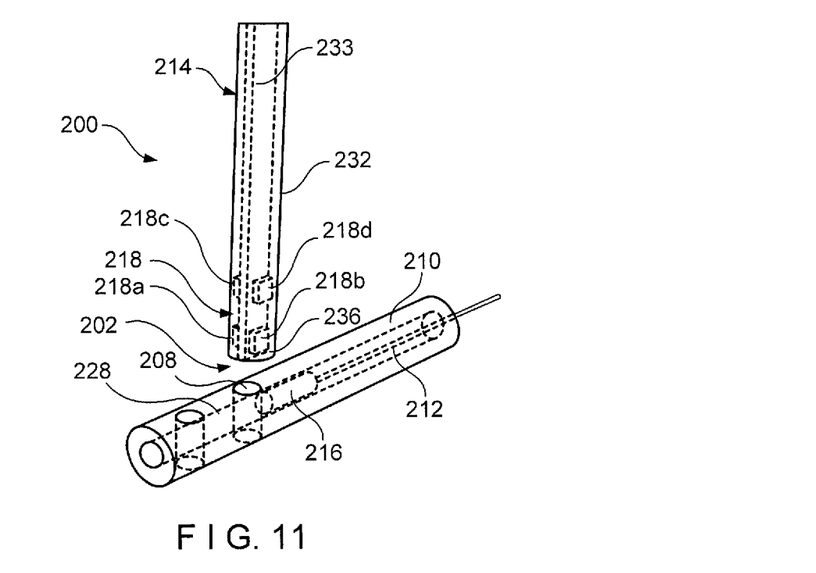
FIG. 11 shows a perspective view of a system according to another exemplary embodiment of the present invention.
Figure 12:
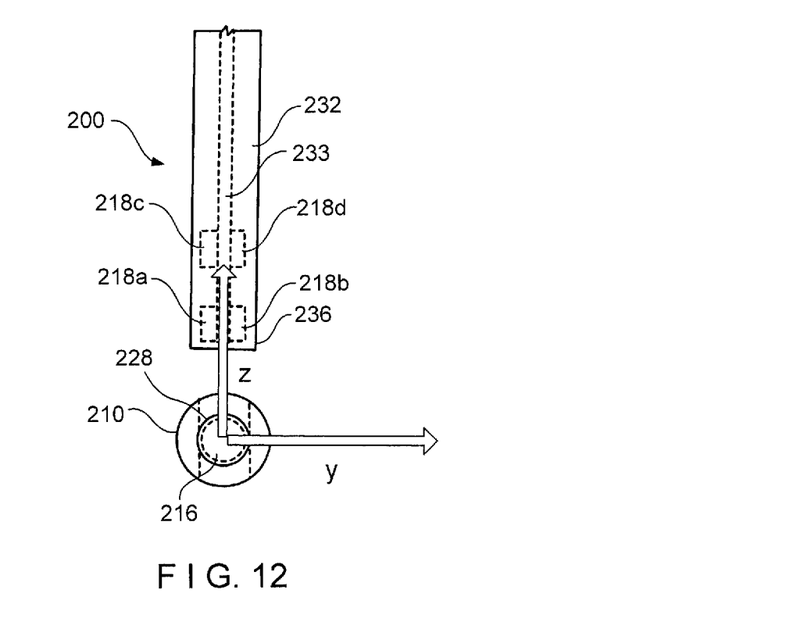
FIG. 12 shows a cross-sectional view of the system of FIG. 11.

As shown in FIGS. 11-12, a system 200 according to another exemplary embodiment of the present invention may be substantially similar to the system 100, comprising an alignment guiding device 202 for aligning an aiming hole of an aiming device and/or a lumen of a guide sleeve with a locking hole 208 of an intramedullary nail 210. The aiming device and guide sleeve may be substantially similar to the aiming device 106 and guide sleeve 130 described above in regard to the system 100. The alignment guiding device 202 may also be substantially similar to the alignment guiding device 102, comprising a first component 212 including a magnet 216 inserted into a longitudinal channel 228 of the intramedullary nail 210 proximate the locking hole 208 and a second component 214 including a sensing unit 218 inserted through the aiming hole and/or guide sleeve to determine the displacement thereof relative to the locking hole 208. The sensing unit 218, however, includes four sensors 218a-218d. First and second sensors 218a, 218b are arranged at a distal end 236 of a probe 232 on opposite sides of the probe 232 and at substantially the same longitudinal position therealong. For example, the first and second sensors 218a, 218b may be secured to a PCB 233 fixed within the probe 232. Third and fourth sensors 218c, 218d are positioned proximally of the first and second sensors 218a, 218b at substantially the same longitudinal position along the PCB 233 relative to one another. The third sensor 218c is positioned on the same side as the first sensor 218a while the fourth sensor 218d is positioned on the same side as the second sensor 218b. Centers of the third and fourth sensors 218c, 218d may be positioned approximately 5-20 mm from the center of the first and second sensors 218a, 218b along the length of the PCB 233.

Figure 15:
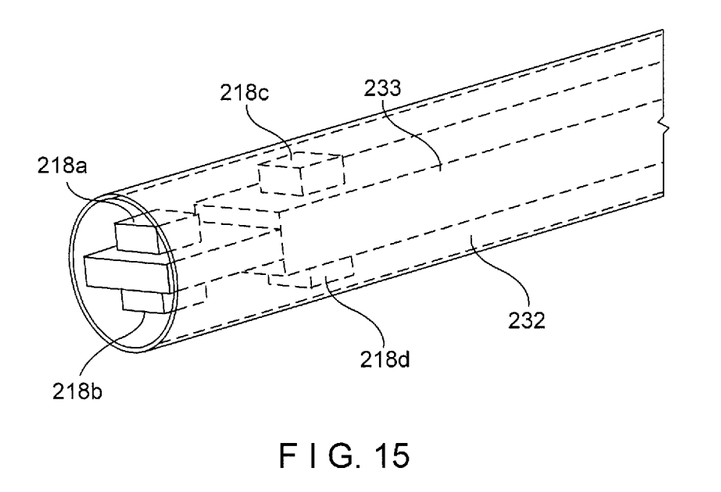
FIG. 15 shows an alternate embodiment of a sensing unit of the system of FIG. 11.

The probe 232 is sized and shaped to be passed through the aiming hole and/or guide sleeve. The probe 232 may, for example, have a diameter of approximately 8 mm. The first and second sensors 218a, 218b may be mounted on opposing sides of the PCB 233 fixed within the probe 232 such that the sensor unit 218 is arranged at a distal end 236 thereof. The PCB 233 may have a width ranging from between 1.6 mm to 5.0 mmm. In one exemplary embodiment, for example, the probe has a width of 3.2 mm. In other words, a transverse distance between the first and second sensors 218a, 218b corresponds to the width of the PCB 233 along which the first and second sensors 218a, 218b are mounted. As shown in FIGS. 11 and 12, the width of the PCB 233 may be constant such that the transverse distance between the first and second sensors 218a, 218b is the same as the transverse distance between the third and fourth sensors 218c, 218d. It will be understood by those of skill in the art, however, that the a width of the PCB 233 may vary along a length thereof such that the transverse distance between the first and second sensors 218a, 218b does not equal the transverse distance between the third and fourth sensors 218c, 218d. For example, as shown in FIG. 15, portion of the PCB 233 on which the first and second sensors 218a, 218b are mounted may have a smaller width than a portion of the PCB 233 on which the third and fourth sensors 218c, 218d are mounted such that the transverse distances therebetween vary. It will be understood by those of skill in the art that the transverse distance between the first and second sensors 218a, 218b and the transverse distance between the third and fourth sensors 218c, 218d may vary so long as a center plane extending therebetween (e.g., a center plane extending through a center of the probe 232 along a length thereof) remains the same. It will also be understood by those of skill in the art that the sensitivity of the sensors 218a-218d will generally increase with larger transverse distances.

Figure 13:
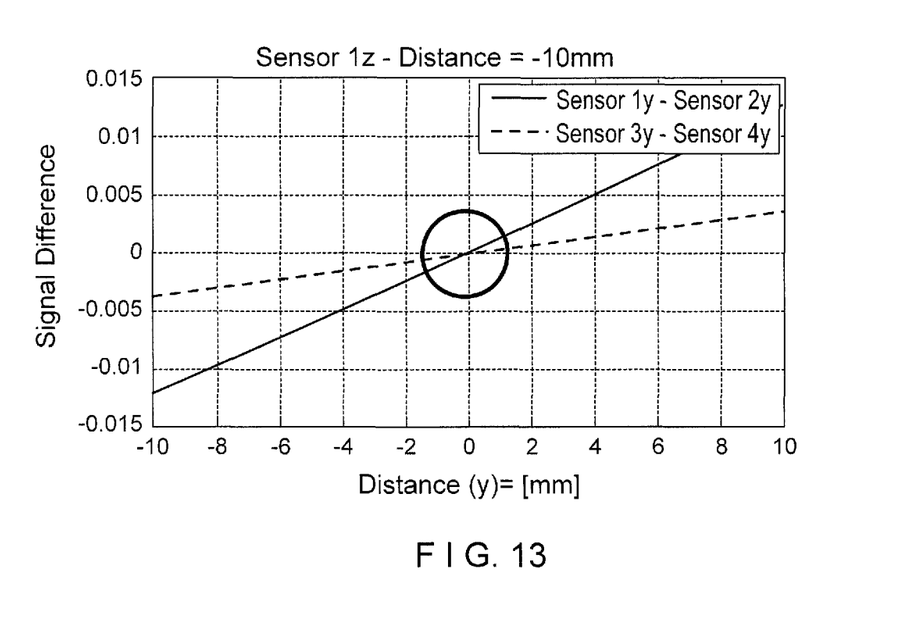
FIG. 13 shows a graph of difference signals having symmetrical fields, according to the system of FIG. 11.

The first and second sensors 218a, 218b are configured to sense a parameter of a magnetic field generated by the magnet 216 in a manner similar to the operation of the first and second sensors 118a, 118b. The third and fourth sensors 218c, 218d detect distortions of the magnetic field. As described above in regard to the sensing unit 118, the sensors 218a-218d may be any combination of 1D, 2D and 3D sensors. In one exemplary embodiment, 3D sensors are employed such that the sensors 218a-218d are not limited to 1 field component and a larger working volume is available. The sensors 218a-218d may include for example a HONEYWELL® 3D magnoresistive sensor, for example a HMC1043 sensor, an ALLEGRO® 1D sensor, for example an A1395 sensor, and/or an AUSTRIAMICROSYSTEMS® 1D sensor, for example an AS5510. When the first sensor 218a is in equilibrium with the second sensor 218b and the third sensor 218c is in equilibrium with the fourth sensor 218d, the system indicates that the probe 232 is in alignment with the locking hole 208. In particular, as shown in FIG. 12, when the probe 232 is aligned with a Z-axis of the magnet 216 and both the first and second sensors 218a, 218b and the third and fourth sensors 218c, 218d are symmetrically distributed along a Y-axis of the magnet 216 (e.g., a difference between a Y position of the first sensor 218a and the Y position of the second sensor 218b=0 and a difference between the Y position of the third sensor 218c and the Y position of the fourth sensor 218d=0), the system indicates that the probe 232, and thereby the guide sleeve and/or aiming hole through which it is inserted, are in alignment with the locking hole 208. For example, as shown in the graph of FIG. 13, the difference signals for both the first and second sensors 218a, 218b and the third and fourth sensors 218c, 218d intersect at Y=0, indicating to a user that proper alignment has been achieved. The alignment may be indicated on a display attached, for example, to a proximal end of the probe 232.

Figure 14:
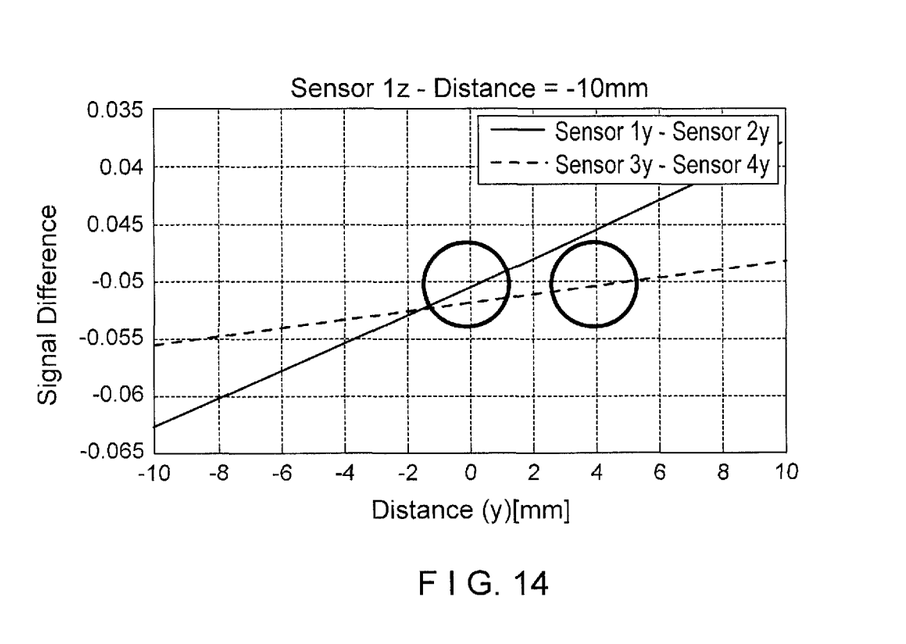
FIG. 14 shows a graph of difference signals having an asymmetrical field distortion, according to the system of FIG. 11.

When the first and second sensors 218a, 218b are in equilibrium but the third and fourth sensors 218c, 218d are not in equilibrium, however, the system indicates that there is an anomaly present such that it is not possible to sense alignment properly. For example, as shown in the graph of FIG. 14, a zero point between the difference signal of first and second sensors 218a, 218b and the difference signal of third and fourth sensors 218c, 218d are not at the same Y-location, indicating that an anomaly is present. The detection of an anomaly may be indicated to the user via a warning signal such as flashing LEDs on the display. The user may then attempt to remove the anomaly until the warning signal is no longer displayed. Once the anomaly has been removed, the user may continue to attempt to find the proper alignment using the technique described above.

Alignment of the probe 232 with the locking hole 208 may be determined in a manner substantially similar to that described above in regard to the system 100. In particular, a Y-component of the magnetic field for all of the four sensors 218a-218d is determined. A first signal difference between the first and second sensors 218a, 218b (e.g., the difference between the Y-components of the first and second sensors 218a, 218b) and a second signal difference between the third and fourth sensors (218c, 218d (e.g., the difference between the Y-components of the third and fourth sensors 218c, 218d) are then calculated. If the signal difference between the first and second sensors 218a, 218b is outside a first threshold range, the display attached to the proximal end of the probe 232 indicates that the aiming device and/or guide sleeve, through which the probe 232 is inserted, should be moved and indicates a direction in which the device should be moved to reduce the difference. If the signal difference is greater than an upper limit of the range (i.e., the difference is a positive value outside the range), the display indicates a first direction in which the device should be moved while, when the difference is less than a lower limit of the range (i.e., the difference is a negative value outside the range), the display indicates that the aiming device and/or guide sleeve should be moved in a second direction.

If the signal difference between the first and second sensors 218a, 218b is within the first threshold range and the signal difference between the third and fourth sensors 218c, 218d is within a second threshold range, the system indicates that the probe 232 and the aiming device and/or guide sleeve are properly aligned with the locking hole 208. If, however, the signal difference between the first and second sensors 218a, 218b is within the first threshold range but the signal difference between the third and fourth sensors 218c, 218d is not within the second threshold range, the display may indicate the probably presence of an anomaly via, for example, a warning signal on the display. The first and second threshold ranges represent a target range. It will be understood by those of skill in the art that since the magnitude of the signal differences depend on the sensor-magnet distance, the first and second threshold ranges are not constant. Rather, the first and second threshold ranges may be a function depending on the magnetic signal strength. It will also be understood by those of skill in the art that although the exemplary embodiment specifically describes calculation of the signal differences using the Y-components, a variety of other configurations are also possible so long as the sensor unit 218 is able to detect alignment and/or disturbance with the locking hole 208.

Figure 16:
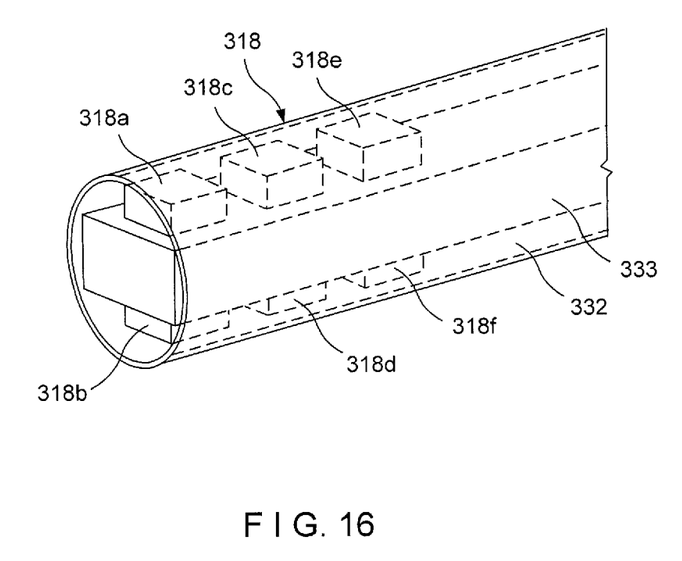
FIG. 16 shows a further embodiment of a sensing unit according to an exemplary embodiment of the present invention.

Although the sensor unit 218 is specifically described as including four sensors 218a-218d, it will be understood by those of skill in the art that the sensor unit 218 may include more than four sensors. For example, as shown in FIG. 16, a sensor unit 318 may include six sensors 318a-318f. The sensors 318a-318d may be substantially similar to the sensors 218a-218d described above in regard to the system 200. The sensor unit 318, however, includes fifth and sixth sensor 318e, 318f which are positioned proximally of the third and fourth sensors 318c, 318d at the same longitudinal position and on opposing sides of a PCB 333 which is fixed within a probe 332. It will be understood by those of skill in the art that the sensor unit 318 may include any number of additional sensors. It will also be understood by those of skill in the art that additional sensors increase an accuracy of the determination of alignment.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A device for aligning an aiming hole of an aiming device with a locking hole of an intramedullary nail, comprising:
a sensing unit comprising a probe and sized and shaped for insertion through a lumen of a guide sleeve inserted through the aiming hole of the aiming device attachable to the intramedullary nail, the sensing unit detecting a magnetic field produced by a magnet and outputting an alignment signal based on a magnetic field parameter at first and second locations relative to the magnet,
wherein a width and length of the probe are selected so that the probe is coaxially insertable through the aiming hole of the aiming device.

2. The device of claim 1, wherein the sensing unit comprises a single sensor, the alignment signal being determined by moving the sensing unit between the first and second locations relative to the magnet.

3. The device of claim 1, wherein the sensing unit includes first and second sensors separated from one another.

4. The device of claim 3, wherein the first and second sensors arc attached to a distal end of the probe.

5. The device of claim 3, wherein the first and second sensors are positioned on opposite sides of the probe.

6. The device of claim 3, wherein the first and second sensors are field sensors for detecting a magnetic field parameter to indicate a target location.

7. The device of claim 6, wherein the first and second sensors are multi-dimensional sensors.

8. The device of claim 3, wherein the sensing unit comprises a third sensor.

9. The device of claim 8, wherein the third sensor is located proximally to the first and second sensors to identify anomalies in the magnetic field.

10. The device of claim 8, wherein the sensing unit comprises a fourth sensor, the third and fourth sensors located proximally of the first and second sensors to detect distortions in the magnetic field.

11. The device of claim 1, further comprising an indicating device indicating a target location of the sensing unit relative to a current location.

12. The device of claim 11, wherein the indicating device includes a first indicator showing a direction of the target location.

13. The device of claim 11, wherein the indicating device includes a second indicator showing an alignment of the current location with the target location.

14. The device of claim 11, wherein the indicating device is coupled to a proximal end of the probe to which the sensing unit is attached.

15. The device of claim 11, wherein the indicating device prevents the sensing unit from being inserted through the aiming hole beyond a desired distance.

16. The device of claim 11, wherein the indicating device includes a third indicator indicating a disturbance error.

17. A system for aligning an aiming hole of an aiming device with a locking hole of an intramedullary nail, comprising:
a magnet sized and shaped for insertion through a channel of an intramedullary nail proximate a locking hole thereof; and
a sensing unit comprising a probe and sized and shaped for insertion through a lumen of a guide sleeve inserted through the aiming hole of the aiming device coupled to the intramedullary nail, the sensing unit detecting from outside a patient's body a magnetic field produced by the magnet inserted through the intramedullary nail inserted into the patient's body and outputting an alignment signal based on a magnetic field parameter at first and second locations relative to the magnet,
wherein a width and length of the probe are selected so that the probe is coaxially insertable through the aiming hole of the aiming device.

18. The system of claim 17, further comprising:
the intramedullary nail sized and shaped for insertion through a medullary canal of a bone, the nail including a channel extending longitudinally therethrough and a locking hole extending transversely therethrough, the locking hole sized and shaped to receive a bone fixation element therethrough; and
an aiming device couplable to the intramedullary nail and including an aiming hole extending therethrough such that when the aiming device is coupled to the intramedullary nail, a central axis of the aiming hole is substantially coaxial with a central axis of the locking hole; and
a guide sleeve sized and shaped for insertion through the aiming hole, the guide sleeve extending longitudinally from a proximal end to a distal end and including a lumen extending therethrough.

19. The system of claim 17, wherein the sensing unit includes first and second sensors attached to a distal end of the probe on opposing sides thereof.

20. The system of claim 19, wherein the sensing unit includes a third sensor attached to the probe, proximally of the first and second sensors.

21. The system of claim 20, wherein the sensing unit includes a fourth sensor attached to the probe proximally of the first and second sensors, the third and fourth sensors attached to opposing sides of the probe to detect a distortion of the magnetic field.

22. The system of claim 17, wherein the sensing unit includes a single sensor which determines the alignment signal via a movement between the first and second locations.

23. The system of claim 17, wherein the magnet is attached to a distal end of a rod having a length corresponding to a desired position of the magnet within the intramedullay nail.

24. A device for aligning an aiming hole of an aiming device with a locking hole of an intramedullary nail, comprising:
a sensing unit sized and shaped for insertion through a lumen of a guide sleeve inserted through the aiming hole of the aiming device attachable to the intramedullary nail, the sensing unit detecting a magnetic field produced by a magnet and outputting an alignment signal based on a magnetic field parameter at first and second locations relative to the magnet.

* * * * *